US009000088B2

(12) United States Patent
Backer et al.

(10) Patent No.: US 9,000,088 B2
(45) Date of Patent: Apr. 7, 2015

(54) HYDROLYSABLE SILANES AND ELASTOMER COMPOSITIONS CONTAINING THEM

(71) Applicant: Dow Corning Corporation, Midland, MI (US)

(72) Inventors: Michael Wolfgang Backer, Mainz (DE); Thomas Chaussee, Fontaines Saint Martin (FR); Damien Deheunynck, Tavaux (FR); Sebastien Grofils, Porcheresse (BE)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 14/362,618

(22) PCT Filed: Dec. 7, 2012

(86) PCT No.: PCT/EP2012/074736
§ 371 (c)(1),
(2) Date: Jun. 4, 2014

(87) PCT Pub. No.: WO2013/083749
PCT Pub. Date: Jun. 13, 2013

(65) Prior Publication Data
US 2014/0364560 A1 Dec. 11, 2014

(30) Foreign Application Priority Data

Dec. 8, 2011 (GB) .................................... 1121122.4

(51) Int. Cl.
| | |
|---|---|
| *C07F 7/02* | (2006.01) |
| *C07F 7/08* | (2006.01) |
| *C07F 7/10* | (2006.01) |
| *C08L 9/00* | (2006.01) |
| *C08C 19/26* | (2006.01) |
| *C07F 7/18* | (2006.01) |
| *C08K 3/36* | (2006.01) |

(52) U.S. Cl.
CPC . *C08C 19/26* (2013.01); *C07F 7/10* (2013.01); *C07F 7/1804* (2013.01); *C08K 3/36* (2013.01)

(58) Field of Classification Search
CPC ............ C08L 9/00; C07F 7/02; C07F 7/0803; C07F 7/081; C07F 7/0812
See application file for complete search history.

(56) References Cited

U.S. PATENT DOCUMENTS

| | | | |
|---|---|---|---|
| 2,853,488 A | 9/1958 | D'Amico et al. | |
| 3,046,250 A * | 7/1962 | Plueddemann | ................. 528/28 |
| 3,147,161 A | 9/1964 | Abere et al. | |
| 3,169,122 A | 2/1965 | Hennes | |
| 3,379,707 A | 4/1968 | Lund et al. | |
| 3,408,198 A | 10/1968 | Reynolds et al. | |
| 3,779,703 A | 12/1973 | Tesoro | |
| 3,810,843 A | 5/1974 | Slusarczuk et al. | |
| 3,855,241 A | 12/1974 | Wilkus et al. | |
| 3,928,330 A | 12/1975 | Ramey et al. | |
| 4,083,861 A | 4/1978 | Seiler et al. | |
| 5,106,680 A | 4/1992 | King et al. | |
| 5,300,641 A * | 4/1994 | Dinh et al. | ..................... 544/229 |
| 5,369,143 A | 11/1994 | Kurimoto et al. | |
| 5,821,277 A | 10/1998 | Hirayama et al. | |
| 5,852,099 A | 12/1998 | Vanel | |
| 6,494,946 B1 | 12/2002 | Belmont et al. | |
| 6,794,428 B2 | 9/2004 | Burrington et al. | |
| 6,806,339 B2 | 10/2004 | Cray et al. | |
| 7,144,967 B2 | 12/2006 | Sakamoto et al. | |
| 7,419,975 B2 | 9/2008 | Palermo et al. | |
| 7,732,029 B1 | 6/2010 | Moorlag et al. | |
| 7,833,404 B2 | 11/2010 | Matsuda et al. | |
| 7,847,117 B2 | 12/2010 | Merget | |
| 7,981,966 B2 | 7/2011 | Kobayashi et al. | |
| 8,140,294 B2 | 3/2012 | Ramey et al. | |
| 8,202,944 B2 | 6/2012 | Suzuki et al. | |
| 8,318,858 B2 | 11/2012 | Oshima | |
| 8,476,375 B2 | 7/2013 | Backer et al. | |
| 8,524,836 B2 | 9/2013 | Kavanagh et al. | |
| 8,569,417 B2 | 10/2013 | Backer et al. | |
| 2005/0234042 A1 | 10/2005 | Palermo et al. | |
| 2010/0056713 A1 | 3/2010 | Oshima | |
| 2010/0099866 A1* | 4/2010 | Honma et al. | .................. 544/69 |
| 2010/0137499 A1 | 6/2010 | Moorlag et al. | |
| 2010/0256273 A1* | 10/2010 | Cruse et al. | ................... 524/262 |
| 2010/0317778 A1* | 12/2010 | Gerster et al. | ................ 524/133 |
| 2011/0049056 A1 | 3/2011 | Wyndham et al. | |
| 2011/0146877 A1 | 6/2011 | Tanaka et al. | |

(Continued)

FOREIGN PATENT DOCUMENTS

| | | |
|---|---|---|
| DE | 206848 | 2/1984 |
| GB | 1123303 | 8/1968 |

(Continued)

OTHER PUBLICATIONS

Matsuo et al: "Introduction of amino groups into the interlayer space of graphite oxide using 3-aminopropylethoxysilanes", Carbon, Elsevier, Oxford, GB, vol. 45, No. 7, Jun. 1, 2007, pp. 1384-1390.
Organometallics, vol. 13(9), 1994, (Muehleisen, Mathias; Tacke, Reinhold), pp. 3740-3742.

(Continued)

*Primary Examiner* — Robert S Loewe
(74) *Attorney, Agent, or Firm* — Matthew T. Fewkes

(57) ABSTRACT

This invention relates to hydrolysable silanes useful in the modification of elastomers, and as coupling agents for diene elastomer compositions containing a filler. In particular the invention relates to novel hydrolysable silanes containing a piperazine ring and an ether or thioether linkage.

20 Claims, No Drawings

(56) References Cited

U.S. PATENT DOCUMENTS

| | | |
|---|---|---|
| 2011/0172367 A1 | 7/2011 | Backer et al. |
| 2012/0059121 A1 | 3/2012 | Backer et al. |
| 2012/0065319 A1 | 3/2012 | Backer et al. |
| 2012/0270997 A1 | 10/2012 | Tanaka et al. |
| 2012/0277369 A1 | 11/2012 | Yoshida et al. |
| 2012/0330044 A1 | 12/2012 | Hou |
| 2013/0079464 A1 | 3/2013 | Nishioka et al. |

FOREIGN PATENT DOCUMENTS

| | | |
|---|---|---|
| GB | 1214451 | 12/1970 |
| GB | 1473335 | 5/1977 |
| HU | 180661 | 4/1983 |
| JP | 5543143 | 3/1980 |
| JP | 10095933 | 4/1998 |
| JP | 2001240706 | 9/2001 |
| JP | 2004085689 | 3/2004 |
| JP | 2004085775 | 3/2004 |
| JP | 2004109586 | 4/2004 |
| JP | 2005249897 | 9/2005 |
| JP | 2008163283 | 7/2008 |
| WO | 9429324 | 12/1994 |
| WO | 0170866 | 9/2001 |
| WO | 2011083050 | 7/2011 |

OTHER PUBLICATIONS

Russian Journal of Applied Chemistry; vol. 82, Issue 5, pp. 928-930; Journal 2009; by V. M. Farzaliev, M. T. Abbasova, A. A. Ashurova, G. B. Babaeva, N. P. Ladokhina and Ya. M. Kerimova.
The Russian Chemical Bulletin, vol. 44(2), 1995, pp. 374-375.
The Vanderbilt Rubber Handbook (1978), pp. 344 through 346.
Journal of Membrane Science, vol. 129(2), 1997, Barbiou, Mihai et al, pp. 197-207.
European Journal of Organic Chemistry, vol. 13, 2006, (Bianco, Alberto et al.), pp. 2934-2941.
Gasparrini, F. et al., "Molecular recognition of p-tert-butylcalixarenes by surface-linked fullerenes C60 and C70", Tetrahedron, Elsevier Science Publishers, Amsterdam, NL, vol. 57, No. 32, Aug. 6, 2001, pp. 6997-7002.
Bianco et al., "Molecular recognition by a silica-bound fullerene derivative", J. Am. Chem. Soc. 1997, vol. 119, pp. 7550-7554.
Brunauer et al., Adsorption of Gases in Multimolecular Layers, Feb. 1938, pp. 309-319, vol. 60.
Chemische Berichte, vol. 120(4), 1987, Brueckmann, Ralf, et al., pp. 635-641.

* cited by examiner

HYDROLYSABLE SILANES AND ELASTOMER COMPOSITIONS CONTAINING THEM

This application is a U.S. national stage filing under 35 U.S.C. §371 of PCT Application No. PCT/EP12/74736 filed on 7 Dec. 2012, currently pending, which claims the benefit of GB Patent Application No. 1121122.4 filed 8 Dec. 2011 under 35 U.S.C. §119 (a)-(d) and 35 U.S.C. §365(a). PCT Application No. PCT/EP12/74736 and GB Patent Application No. 1121122.4 are hereby incorporated by reference.

This invention relates to hydrolysable silanes useful in the modification of elastomers, and as coupling agents for diene elastomer compositions containing a filler. In particular the invention relates to novel hydrolysable silanes containing a piperazine ring and an ether or thioether linkage.

WO-A-2010/139473 describes various hydrolysable silanes as coupling agents between an inorganic filler and an elastomer. The silanes include those containing a heterocyclic ring such as N-(3-triethoxysilylpropyl)-dihydroimidazole and 1-(3-triethoxysilylpropyl)-pyrrole.

Other examples of hydrolysable silanes which have been proposed as coupling agents include unsaturated silanes containing an ester group, such as an acryloxypropyltrialkoxysilane, described in WO-A-2010/125124.

WO2011/040312, Organometallics, Vol. 13(9), 1994, pages 3740-2 and U.S. Pat. No. 3,779,703 describe piperazyl bis-silane compounds.

U.S. Pat. No. 3,810,843 describes (3,3'-[N,N'-piperazyl]-bis-[propyltrimethoxysilane].

WO94/29324 describes an amidopiperazylsilane.

A hydrolysable silane according to the present invention has the formula

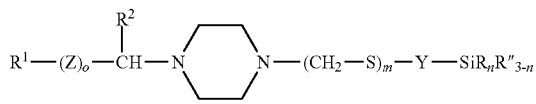

wherein each R represents a hydrolysable group; each R" represents a hydrocarbyl group having 1 to 8 carbon atoms; n=1 to 3; Y represents a divalent organic spacer linkage having 1 to 20 carbon atoms; m=0 or 1; the piperazine ring is optionally substituted on his C atoms; Z represents an oxygen or sulphur atom; n is 0 or 1; o is 0 or 1; $R^1$ represents a hydrocarbyl or substituted hydrocarbyl group having 1 to 20 carbon atoms; $R^2$ represents hydrogen or a hydrocarbyl or substituted hydrocarbyl group having 1 to 8 carbon atoms and m+o is 1 or 2.

A process according to the invention for modifying a polymeric material having a carbon backbone containing carbon-to-carbon unsaturation by reaction with a hydrolysable silane is characterised in that the hydrolysable silane is a hydrolysable silane as defined above. The polymeric material can for example be a hydrocarbon polymer containing ethylenic unsaturation such as a diene elastomer.

The hydrolysable silanes of the invention are capable of bonding strongly to diene elastomers under the processing conditions used for producing elastomer products such as tyres. Preferably, o is 1. We believe that upon heating to the temperatures used in elastomer processing, the etheramine or thioetheramine moiety of the hydrolysable silanes of the invention forms a very reactive species which reacts with the C=C bonds present in diene elastomers through [2+3] cycloaddition. The hydrolysable silanes of the invention are also capable of bonding strongly to fillers having surface hydroxyl groups through hydrolysis of the silane group, thus forming very effective coupling agents.

The invention includes a diene elastomer composition comprising a diene elastomer, a hydrolysable silane and a curing agent for the diene elastomer, characterised in that the hydrolysable silane is a hydrolysable silane of the formula

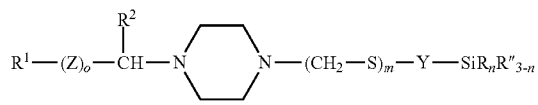

as defined above. A process according to the invention for the production of a rubber article is characterized in that such a diene elastomer composition is shaped and cured.

The invention also includes the use of a hydrolysable silane of the formula

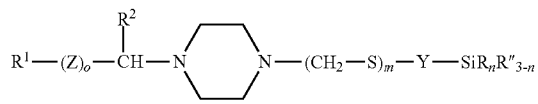

as defined above as a coupling agent for a diene elastomer composition containing a filler.

Hydrolysable silanes in which n=3 may be preferred as having the maximum number of hydrolysable groups. Examples of groups of the formula $R_aR'_{3-a}Si-A$ in which a=3 include trialkoxysilylalkyl groups such as triethoxysilylalkyl or trimethoxysilylalkyl groups, or triacetoxysilylalkyl groups. However hydrolysable silanes in which a=2 or a=1 are also useful coupling agents. In such hydrolysable silanes the group R' is a hydrocarbyl group having 1 to 8 carbon atoms. Preferred groups R' include alkyl groups having 1 to 4 carbon atoms such as methyl or ethyl, but R' can be an alkyl group having more carbon atoms such as hexyl or 2-ethylhexyl or can be an aryl group such as phenyl. Examples of groups of the formula $R_aR'_{3-a}Si-A$ in which a=2 include diethoxymethylsilylalkyl, diethoxyethylsilylalkyl, dimethoxymethylsilylalkyl or diacetoxymethylsilylalkyl groups.

Hydrolysable silanes in which the group R is an ethoxy group are often preferred. The alcohol or acid RH may be released when the silane is hydrolysed, and ethanol is the most environmentally friendly compound among the alcohols and acids.

In the group of the formula —Y—SiR$_n$R"$_{3-n}$, Y represents a divalent organic spacer linkage having 1 to 20 carbon atoms. Preferably Y has 2 to 20 carbon atoms. Y can conveniently be an alkylene group, particularly an alkylene group having 2 to 6 carbon atoms. Preferred examples of linkage Y are —(CH$_2$)$_3$—, —(CH$_2$)$_4$—, and —CH$_2$CH(CH$_3$)CH$_2$-groups. The group of the formula $R_aR'_{3-a}Si-A$ can for example be a 3-(triethoxysilyl)propyl, 4-(triethoxysilyl)butyl, 2-methyl-3-(triethoxysilyl)propyl, 3-(trimethoxysilyl)propyl, 3-triacetoxysilylpropyl, 3-(diethoxymethylsilyl)propyl, 3-(diethoxyethylsilyl)propyl or 3-(diacetoxymethylsilyl)propyl group.

The hydrolysable silane of the formula

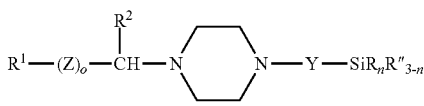

as defined above can in general be prepared by reacting a 1-silylalkyl-piperazine of the formula H-Pip-Y—SiR$_n$R"$_{3-n}$, wherein R, R", n, and Y are defined as above, with an aldehyde of the formula R$^2$—CHO wherein R$^2$ represents hydrogen or a hydrocarbyl or substituted hydrocarbyl group having 1 to 8 carbon atoms and an alcohol or thiol of the formula R$^1$ZH wherein Z represents an oxygen or sulphur atom; and R$^1$ represents a hydrocarbyl or substituted hydrocarbyl group having 1 to 20 carbon atoms.

The 1-silylalkyl-piperazine of the formula H-Pip-Y—SiR$_n$R"$_{3-n}$ can for example be prepared by reacting a 1-alkenyl-piperazine with an alkoxysilane containing a Si—H group of the formula HSiR$_n$R"$_{3-n}$. For example 1-(3-triethoxysilylpropyl)-piperazine can be prepared by the reaction of 1-allyl-piperazine with HSi(OC$_2$H$_5$)$_3$.

In one preferred group of hydrolysable silanes according to the invention, Z represents sulphur and the group R$^1$ contains an anchoring group whereby any thiol liberated will remain chemically bound in the elastomer composition. Most preferably the group R$^1$ contains a hydrolysable silane group, since hydrolysable silane groups are capable of bonding strongly to fillers through hydrolysis of the silane group. When Z represents sulphur, the group R$^1$ is preferably not a simple alkyl group since a malodorous alkylthiol may then be liberated during reaction with the C=C bonds present in diene elastomers upon heating to the temperatures used in elastomer processing. R$^1$ can for example be a group of the formula —Y'—SiR$_p$R"$_{3-p}$ wherein Y' represents a divalent organic spacer linkage having 1 to 20 carbon atoms; each R represents a hydrolysable group; each R" represents a hydrocarbyl group having 1 to 8 carbon atoms; and p=1 to 3. The thiol R$^1$SH can for example be HS—(CH$_2$)$_3$—Si(OC$_2$H$_5$)$_3$.

When R$^1$ is a group of the formula —Y'—SiR$_p$R"$_{3-p}$ it may be preferred that m=1. Y and Y' may then each represent an alkylene group having 2 to 6 carbon atoms. The hydrolysable silane of the invention can thus be of the formula

wherein each R represents a hydrolysable group; each R" represents a hydrocarbyl group having 1 to 8 carbon atoms; n=1 to 3; and Y represents a divalent organic spacer linkage having 1 to 20 carbon atoms. In a preferred process according to the invention such a hydrolysable silane can be prepared by reacting a thioalkyl alkoxysilane of the formula HS—Y—SiR$_n$R"$_{3-n}$, wherein R, R", n, and Y are defined as above, with piperazine and formaldehyde.

The hydrolysable silane of the invention can for example be

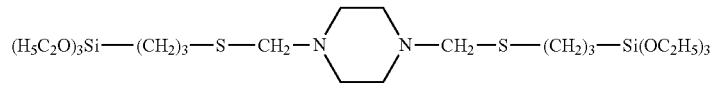

which can be prepared by the reaction of 3-mercaptopropyl-triethoxysilane with piperazine and formaldehyde.

A hydrolysable silane of the invention in which Z represents sulphur and the group R$^1$ is of the formula —Y'—SiR$_p$R"$_{3-p}$ can alternatively have m=0, for example it can be of the formula

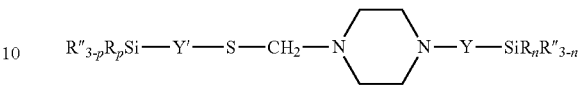

wherein each R represents a hydrolysable group; each R" represents a hydrocarbyl group having 1 to 8 carbon atoms; n=1 to 3; p=1 to 3; and Y and Y' each represent a divalent organic spacer linkage having 1 to 20 carbon atoms, for example an alkylene group having 2 to 6 carbon atoms. Such a hydrolysable silane can be prepared by the reaction of a 1-silylalkyl-piperazine of the formula H-Pip-Y—SiR$_n$R"$_{3-n}$ with a thioalkyl alkoxysilane of the formula HS—Y'—SiR$_p$R"$_{3-p}$ and formaldehyde.

The hydrolysable silane of the invention can for example be

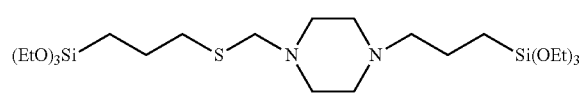

where Et represents an ethyl group, which can be prepared by the reaction of 1-(3-triethoxysilylpropyl)-piperazine with 3-mercaptopropyltriethoxysilane and formaldehyde.

In the hydrolysable silanes according to the invention of the formula

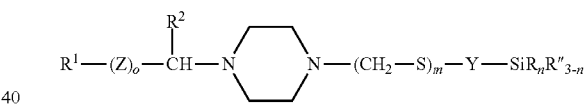

in which Z represents an oxygen atom, R$^1$ preferably represents a hydrocarbyl group having 1 to 8 carbon atoms. Such silanes can be formed by reaction of an alcohol of the formula R$^1$OH with a 1-silylalkyl-piperazine and an aldehyde R$^2$—CHO. The aldehyde is preferably formaldehyde, wherein R$^2$ represents hydrogen. The formaldehyde can for example be added to the reaction in the form of paraformaldehyde. Alternative aldehydes include acetaldehyde and butyraldehyde. Examples of suitable alcohols include ethanol, methanol, propanol, n-butanol, 2-methylpropanol, t-butanol, n-hexanol and 2-ethylhexanol. The alcohol can act as both solvent and reagent in the reaction with the 1-silylalkyl-piperazine and aldehyde.

The most preferred alcohol is ethanol, i.e. R$^1$ is preferably ethyl. When the hydrolysable silane of the invention reacts with the C=C bonds present in diene elastomers through [2+3] cycloaddition, an alcohol of the formula R$^1$OH may be liberated. Ethanol is preferred as the most environmentally friendly alcohol.

The hydrolysable silane of the invention can for example be

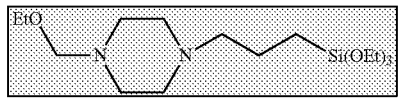

where Et represents an ethyl group, which can be prepared by the reaction of 1-(3-triethoxysilylpropyl)-piperazine with ethanol and formaldehyde.

The alcohol $R^1OH$ which is reacted with a 1-silylalkyl-piperazine and an aldehyde can alternatively be of the formula $HO-((CH2)_aO)_b-R^3$ wherein a=1 to 3; b=1 to 6; and $R^3$ represents hydrogen or a hydrocarbyl or substituted hydrocarbyl group having 1 to 20 carbon atoms. In this case the alcohol $R^1OH$ is a diol such as ethylene glycol or propylene glycol, a polyoxyalkylene glycol such as polyoxyethylene glycol or polyoxypropylene glycol, an etheralcohol such as ethoxyethanol or methoxyethanol or a polyoxyalkylene glycol monoether such as ethoxyethoxyethanol.

When the alcohol $R^1OH$ is an etheralcohol or a polyoxyalkylene glycol monoether, reaction with a 1-silylalkyl-piperazine of the formula $H-Pip-Y-SiR_nR''_{3-n}$ and an aldehyde of the formula $R^2-CHO$ forms a hydrolysable silane of the formula

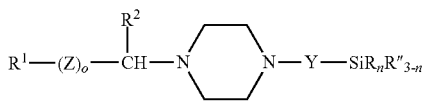

wherein $R^1$ represents an alkoxyalkyl group or poly(alkoxy)alkyl group. When the alcohol $R^1OH$ is a diol or a polyoxyalkylene glycol, reaction with a 1-silylalkyl-piperazine and an aldehyde can also form a bis(silylalkylaminoalkyl) ether by reaction of both alcohol groups of the diol or polyoxyalkylene glycol, if the diol or polyoxyalkylene glycol is used in stoichiometric excess. Reaction of a diol or polyoxyalkylene glycol of the formula $-((CH2)_aO)_b-R^3$, wherein a=1 to 3; b=1 to 6; and $R^3$ represents hydrogen, with a 1-silylalkyl-piperazine of the formula $H-Pip-Y-SiR_nR''_{3-n}$ and formaldehyde can form a bis(silylalkylaminoalkyl) ether of the formula

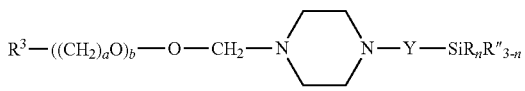

The reaction product of the diol or polyoxyalkylene glycol with the 1-silylalkyl-piperazine and formaldehyde may be a mixture of such a bis(silylalkylaminoalkyl) ether and a hydrolysable silane of the formula $R^1-Z-CH-Pip-Y-SiR_nR''_{3-n}$ wherein $R^3$ represents a hydroxyalkyl group or poly(alkoxy)alkyl group of the formula $-((CH2)_aO)_b-H$.

The piperazine ring can be substituted for example it can be 2-methyl-piperazine, 2,5 dimethylpiperazine, 2, 2 dimethyl-piperazine or 2-carboxylic acid-piperazine.

The hydrolysable silane of the invention can be partially hydrolysed and condensed into oligomers containing siloxane linkages. For most end uses it is preferred that such oligomers still contain at least one hydrolysable group bonded to Si per unsaturated silane monomer unit to enhance coupling of the unsaturated silane, or the polymeric material modified with the unsaturated silane, with fillers having surface hydroxyl groups.

The polymeric material having a carbon backbone containing carbon-to-carbon unsaturation and the hydrolysable silane of the invention are preferably heated together at a temperature of at least 80° C., more preferably to a temperature between 90° C. and 200° C., most preferably between 120° C. and 180° C. The polymeric material and the hydrolysable silane can be mixed followed by a separate heating step, or mixing and heating can be carried out together.

The preferred polymeric material is a hydrocarbon polymer containing ethylenic unsaturation such as a diene elastomer, but the hydrolysable silane of the invention can also be used to modify other polymeric material having a carbon backbone containing carbon-to-carbon unsaturation such as carbon fibre, carbon black, carbon nanotubes or graphene. When the polymeric material is an elastomer, mixing and heating are preferably carried out together so that the elastomer is subjected to mechanical working while it is heated.

In the diene elastomer compositions of the invention, the diene elastomer can be natural rubber. We have found that the hydrolysable silanes of the invention react readily with natural rubber under the processing conditions used for producing rubber products such as tyres and also act as an effective coupling agent in a curable filled natural rubber composition.

The diene elastomer can alternatively be a synthetic polymer which is a homopolymer or copolymer of a diene monomer (a monomer bearing two double carbon-carbon bonds, whether conjugated or not). Preferably the elastomer is an "essentially unsaturated" diene elastomer, that is a diene elastomer resulting at least in part from conjugated diene monomers, having a content of members or units of diene origin (conjugated dienes) which is greater than 15 mol %. More preferably it is a "highly unsaturated" diene elastomer having a content of units of diene origin (conjugated dienes) which is greater than 50 mol %. Diene elastomers such as butyl rubbers, copolymers of dienes and elastomers of alpha-olefins of the ethylene-propylene diene monomer (EPDM) type, which may be described as "essentially saturated" diene elastomers having a low (less than 15 mol %) content of units of diene origin are less preferred.

The diene elastomer can for example be:
(a) any homopolymer obtained by polymerization of a conjugated diene monomer having 4 to 12 carbon atoms;
(b) any copolymer obtained by copolymerization of one or more dienes conjugated together or with one or more vinyl aromatic compounds having 8 to 20 carbon atoms;
(c) a ternary copolymer obtained by copolymerization of ethylene, of an α-olefin having 3 to 6 carbon atoms with a non-conjugated diene monomer having 6 to 12 carbon atoms, such as, for example, the elastomers obtained from ethylene, from propylene with a non-conjugated diene monomer of the aforementioned type, such as in particular 1,4-hexadiene, ethylidene norbornene or dicyclopentadiene;
(d) a copolymer of isobutene and isoprene (butyl rubber), and also the halogenated, in particular chlorinated or brominated, versions of this type of copolymer.

Suitable conjugated dienes include 1,3-butadiene, 2-methyl-1,3-butadiene, 2,3-di(Ci-C5 alkyl)-1,3-butadienes such as, for instance, 2,3-dimethyl-1,3-butadiene, 2,3-diethyl-1,3-butadiene, 2-methyl-3-ethyl-1,3-butadiene, 2-methyl-3-isopropyl-1,3-butadiene, an aryl-1,3-butadiene, 1,3-pentadiene and 2,4-hexadiene.

Suitable vinyl aromatic compounds are, for example, styrene, ortho-, meta- and para-methylstyrene, the commercial mixture "vinyltoluene", para-tert.-butylstyrene, methoxystyrenes, chlorostyrenes, vinylmesitylene, divinylbenzene and vinylnaphthalene. The copolymers may contain between 99% and 20% by weight of diene units and between 1% and 80% by weight of vinyl aromatic units. The elastomers may have any microstructure, which is a function of the polymerization conditions used, in particular of the presence or absence of a modifying and/or randomizing agent and the quantities of modifying and/or randomizing agent used. The elastomers may for example be block, statistical, sequential or microsequential elastomers, and may be prepared in dispersion or in solution; they may be coupled and/or starred or alternatively functionalized with a coupling and/or starring or functionalizing agent. Examples of preferred block copolymers are styrene-butadiene-styrene (SBS) block copolymers and styrene-ethylene/butadiene-styrene (SEBS) block copolymers.

The elastomer can be an alkoxysilane-terminated diene polymer or a copolymer of the diene and an alkoxy-containing molecule prepared via a tin coupled solution polymerization.

When preparing a filled elastomer composition, the elastomer and the hydrolysable silane can be reacted and then mixed with the filler, but the filler is preferably present during the reaction between the elastomer and the unsaturated silane. The elastomer, the silane, the filler and the radical initiator can all be loaded to the same mixer and mixed while being heated, for example by thermo-mechanical kneading. Alternatively the filler can be pre-treated with the hydrolysable silane and then mixed with the elastomer and the radical initiator, preferably under heating. When the hydrolysable silane and radical generator are present during thermo-mechanical kneading of the diene elastomer and the filler, the silane reacts with the elastomer to form a modified diene elastomer and also acts as a coupling agent bonding the filler to the elastomer.

The filler is preferably a reinforcing filler. Examples of reinforcing fillers are silica, silicic acid, carbon black, or a mineral oxide of aluminous type such as alumina trihydrate or an aluminium oxide-hydroxide, or a silicate such as an aluminosilicate, or a mixture of these different fillers.

Use of an unsaturated silane according to the invention is particularly advantageous in a curable elastomer composition comprising a filler containing hydroxyl groups, particularly in reducing the mixing energy required for processing the rubber composition and improving the performance properties of products formed by curing the rubber composition. The hydroxyl-containing filler can for example be a mineral filler, particularly a reinforcing filler such as a silica or silicic acid filler, as used in white tire compositions, or a metal oxide such as a mineral oxide of aluminous type such as alumina trihydrate or an aluminium oxide-hydroxide, or carbon black pre-treated with a alkoxysilane such as tetraethyl orthosilicate, or a silicate such as an aluminosilicate or clay, or cellulose or starch, or a mixture of these different fillers.

The reinforcing filler can for example be any commonly employed siliceous filler used in rubber compounding applications, including pyrogenic or precipitated siliceous pigments or aluminosilicates. Precipitated silicas are preferred, for example those obtained by the acidification of a soluble silicate, e.g., sodium silicate. The precipitated silica preferably has a BET surface area, as measured using nitrogen gas, in the range of about 20 to 600 $m^2/g$, more usually in a range of about 40 or 50 to about 300 $m^2/g$. The BET method of measuring surface area is described in the Journal of the American Chemical Society, Volume 60, Page 309 (1938). The silica may also be typically characterized by having a dibutylphthalate (DBP) value in a range of about 100 to about 350 $cm^3/100$ g, and more usually about 150 to about 300 $cm^3/100$ g, measured as described in ASTM D2414. The silica, and the alumina or aluminosilicate if used, preferably have a CTAB surface area in a range of about 100 to about 220 $m^2/g$ (ASTM D3849). The CTAB surface area is the external surface area as evaluated by cetyl trimethylammonium bromide with a pH of 9. The method is described in ASTM D 3849.

Various commercially available silicas may be considered for use in elastomer compositions according to this invention such as silicas commercially available from Rhodia with, for example, designations of Zeosil® 1165MP, 1115MP, or HRS 1200MP; 200MP premium, 80GR or equivalent silicas available from PPG Industries with designations Hi-Sil® EZ150G, 210, 243, etc; silicas available from Degussa AG with, for example, designations VN3, Ultrasil® 7000 and Ultrasil 7005, and silicas commercially available from Huber having, for example, a designation of Hubersil® 8745 and Hubersil 8715. Treated precipitated silicas can be used, for example the aluminium-doped silicas described in EP-A-735088.

If alumina is used in the elastomer compositions of the invention, it can for example be natural aluminium oxide or synthetic aluminium oxide (Al2O3) prepared by controlled precipitation of aluminium hydroxide. The reinforcing alumina preferably has a BET surface area from 30 to 400 $m^2/g$, more preferably between 60 and 250 $m^2/g$, and an average particle size at most equal to 500 nm, more preferably at most equal to 200 nm. Examples of such reinforcing aluminas are the aluminas A125, CR125, D65CR from Baiotakowski.

Examples of aluminosilicates which can be used in the elastomer compositions of the invention are Sepiolite, a natural aluminosilicate which might be obtained as PANSIL® from Tolsa S.A., Toledo, Spain, and SILTEG®, a synthetic aluminosilicate from Degussa GmbH.

The hydroxyl-containing filler can alternatively be talc, magnesium dihydroxide or calcium carbonate, or a natural organic filler such as cellulose fibre or starch. Mixtures of mineral and organic fillers can be used, as can mixtures of reinforcing and non-reinforcing fillers.

The filler can additionally or alternatively comprise a filler which does not have hydroxyl groups at its surface, for example a reinforcing filler such as carbon black and/or a non-reinforcing filler such as calcium carbonate.

The hydrolysable silane of the invention is preferably present in the diene elastomer composition at least 0.2% by weight based on the diene elastomer and can be up to 20% or more. Preferably the hydrolysable silane is present at 0.5 to 15.0% by weight based on the diene elastomer during thermal processing of the elastomer composition, most preferably 0.5 to 10.0%.

Curing of the diene elastomer composition of the invention can be carried out as a batch process or as a continuous process using any suitable apparatus.

Continuous processing can be effected in an extruder such as a single screw or twin screw extruder. The extruder is preferably adapted to mechanically work, that is to knead or compound, the materials passing through it, for example a twin screw extruder. One example of a suitable extruder is that sold under the trade mark ZSK from Coperion Werner Pfleiderer. The extruder preferably includes a vacuum port shortly before the extrusion die to remove any unreacted silane. The residence time of the diene elastomer, the unsaturated silane and the free radical initiator at above 100° C. in the extruder or other continuous reactor is generally at least 0.5 minutes and preferably at least 1 minute and can be up to 15 minutes. More preferably the residence time is 1 to 5 minutes.

A batch process can for example be carried out in an internal mixer such as a Banbury mixer or a Brabender Plastograph (Trade Mark) 350S mixer equipped with roller blades. An external mixer such as a roll mill can be used for either batch or continuous processing. In a batch process, the elastomer, the unsaturated silane and the free radical initiator are generally mixed together at a temperature above 100° C. for at least 1 minute and can be mixed for up to 20 minutes, although the time of mixing at high temperature is generally 2 to 10 minutes.

The elastomer compositions are preferably produced using the conventional two successive preparation phases of mechanical or thermo-mechanical mixing or kneading ("non-productive" phase) at high temperature, followed by a second phase of mechanical mixing ("productive" phase) at lower temperature, typically less than 110° C., for example between 40° C. and 100° C., during which the cross-linking and vulcanization systems are incorporated.

During the non-productive phase, the unsaturated silane, the diene elastomer, the filler and the radical generator are mixed together. Mechanical or thermo-mechanical kneading occurs, in one or more steps, until a maximum temperature of 110° C. to 190° C. is reached, preferably between 130° C. and 180° C. When the apparent density of the reinforcing inorganic filler is low (generally the case for silica), it may be advantageous to divide the introduction thereof into two or more parts in order to improve further the dispersion of the filler in the rubber. The total duration of the mixing in this non-productive phase is preferably between 2 and 10 minutes.

After cooling of the mixture thus obtained, the curing system is then incorporated at low temperature, typically on an external mixer such as an open mill, or alternatively on an internal mixer (Banbury type). The entire mixture is then mixed (productive phase) for several minutes, for example between 2 and 10 minutes.

The curing agent for the elastomer composition can for example be a conventional sulfur vulcanizing agent. Examples of suitable sulfur vulcanizing agents include, for example, elemental sulfur (free sulfur) or sulfur donating vulcanizing agents, for example, an amine disulfide, polymeric polysulfide or sulfur olefin adducts which are conventionally added in the final, productive, rubber composition mixing step. Preferably, in most cases, the sulfur vulcanizing agent is elemental sulfur. Sulfur vulcanizing agents are used in an amount ranging from about 0.4 to about 8% by weight based on elastomer, preferably 1.5 to about 3%, particularly 2 to 2.5%.

Accelerators are generally used to control the time and/or temperature required for vulcanization and to improve the properties of the vulcanized elastomer composition. In one embodiment, a single accelerator system may be used, i.e., primary accelerator. Conventionally and preferably, a primary accelerator(s) is used in total amounts ranging from about 0.5 to about 4% by weight based on elastomer, preferably about 0.8 to about 1.5%. In another embodiment, combinations of a primary and a secondary accelerator might be used with the secondary accelerator being used in smaller amounts of about 0.05 to about 3% in order to activate and to improve the properties of the vulcanisate. Delayed action accelerators may be used which are not affected by normal processing temperatures but produce a satisfactory cure at ordinary vulcanization temperatures. Suitable types of accelerators that may be used in the present invention are amines, disulfides, guanidines, thioureas, thiazoles, for example mercaptobenzothiazole, thiurams, sulfenamides, dithiocarbamates, thiocarbonates, and xanthates. Preferably, the primary accelerator is a sulfenamide. If a second accelerator is used, the secondary accelerator is preferably a guanidine, dithiocarbamate or thiuram compound. Vulcanization retarders can also be used, for example phthalic anhydride, benzoic acid or cyclohexylthiophthalimide.

The curable diene elastomer composition can contain another coupling agent in addition to the hydrolysable silane of the invention, for example a trialkoxy, dialkoxy or monoalkoxy silane coupling agent, particularly a sulfidosilane or mercaptosilane or an azosilane, acrylamidosilane, blocked mercaptosilane, aminosilane alkylsilane or alkenylsilane having 1 to 20 carbon atoms in the alkyl group and 1 to 6 carbon atoms in the alkoxy group. Examples of preferred coupling agents include a bis(trialkoxysilylpropyl)disulfane or tetrasulfane as described in U.S. Pat. No. 5,684,171, or a bis(dialkoxymethylsilylpropyl)disulfane or tetrasulfane such as bis(methyldiethoxysilylpropyl)tetrasulfane or disulfane, or a bis(dimethylethoxysilylpropyl)oligosulfane, or a dimethylhydroxysilylpropyl dimethylalkoxysilylpropyl oligosulfane as described in WO-A-2007/061550, or a mercaptosilane such as triethoxysilylpropylmercaptosilane. Such a coupling agent promotes bonding of the filler to the organic elastomer, thus enhancing the physical properties of the filled elastomer. The filler can be pre-treated with the coupling agent or the coupling agent can be added to the mixer with the elastomer and filler and the unsaturated silane according to the invention. We have found that use of the hydrolysable silane of this invention in conjunction with such a coupling agent can reduce the mixing energy required for processing the elastomer composition and improve the performance properties of products formed by curing the elastomer composition compared to compositions containing the coupling agent without the hydrolysable silane of the invention.

The elastomer composition can be compounded with various commonly-used additive materials such as processing additives, for example oils, resins including tackifying resins, silicas, and plasticizers, fillers, pigments, fatty acid, zinc oxide, waxes, antioxidants and antiozonants, heat stabilizers, UV stabilizers, dyes, pigments, extenders and peptizing agents.

Typical amounts of tackifier resins, if used, comprise about 0.5 to about 10% by weight based on elastomer, preferably 1 to 5%. Typical amounts of processing aids comprise about 1 to about 50% by weight based on elastomer. Such processing aids can include, for example, aromatic, naphthenic, and/or paraffinic processing oils.

Typical amounts of antioxidants comprise about 1 to about 5% by weight based on elastomer. Representative antioxidants may be, for example, N-1,3-dimethylbutyl-N-phenyl-para-phenylenediamine, sold as "Santoflex 6-PPD"® from Flexsys, diphenyl-p-phenylenediamine and others, for example those disclosed in The Vanderbilt Rubber Handbook (1978), Pages 344 through 346. Typical amounts of antiozonants also comprise about 1 to 5% by weight based on elastomer.

Typical amounts of fatty acids, if used, which can include stearic acid or zinc stearate, comprise about 0.1 to about 3% by weight based on elastomer. Typical amounts of zinc oxide comprise about 0 to about 5% by weight based on elastomer alternatively 0.1 to 5%.

Typical amounts of waxes comprise about 1 to about 5% by weight based on elastomer. Microcrystalline and/or crystalline waxes can be used.

Typical amounts of peptizers comprise about 0.1 to about 1% by weight based on elastomer. Typical peptizers may for example be pentachlorothiophenol or dibenzamidodiphenyl disulfide.

The diene elastomer composition of the invention containing a curing agent is shaped and cured into an article. The elastomer composition can be used to produce tyres, including any part thereof such as the bead, apex, sidewall, inner liner, tread or carcass. The elastomer composition can alternatively be used to produce any other engineered rubber goods, for example bridge suspension elements, hoses, belts, shoe soles, anti seismic vibrators, and dampening elements. The elastomer composition can be cured in contact with reinforcing elements such as cords, for example organic polymer cords such as polyester, nylon, rayon, or cellulose cords, or steel cords, or fabric layers or metallic or organic sheets.

When a sulphur curing system is used the vulcanization, or curing, of a rubber product such as a tire or tire tread is carried out in known manner at temperatures preferably between 130° C. and 200° C., under pressure, for a sufficiently long period of time. The required time for vulcanization may vary for example between 5 and 90 minutes.

The elastomer composition of the invention is particularly advantageous for use in producing a tyre for a heavy vehicle such as a truck. Preferred elastomers for this use are isoprene elastomers; that is an isoprene homopolymer or copolymer, in other words a diene elastomer selected from the group consisting of natural rubber (NR), synthetic polyisoprenes (IR), the various isoprene copolymers or a mixture of these elastomers. Isoprene copolymers include isobutene-isoprene copolymers (butyl rubber-IIR), isoprene-styrene copolymers (SIR), isoprene-butadiene copolymers (BIR) and isoprene-butadiene-styrene copolymers (SBIR). The isoprene elastomer is most preferably natural rubber or a synthetic cis-1,4 polyisoprene; of these synthetic polyisoprenes, preferably polyisoprenes having a content (mole %) of cis-1,4 bonds greater than 90%, more preferably still greater than 98%, are used. For such a tyre for a heavy vehicle, the elastomer may also be constituted, in its entirety or in part, of another highly unsaturated elastomer such as, for example, an SBR or a BR elastomer. The hydrolysable silane of the invention disperses silica into Natural Rubber to form an elastomer composition for truck tyres whereby tyres made from the composition have reduced rolling resistance with maintained wear compared to known tyres containing carbon black as reinforcing filler.

The elastomer composition of the invention can alternatively be used for a passenger car tire, in which case the preferred starting diene elastomer is for example a styrene butadiene rubber (SBR), for example an SBR prepared in emulsion ("ESBR") or an SBR prepared in solution ("SSBR"), or an SBR/BR, SBR/NR (or SBR/IR), alternatively BR/NR (or BR/IR), or SIBR (isoprene-butadiene-styrene copolymers), IBR (isoprene-butadiene copolymers), or blends (mixtures) thereof.

When the elastomer composition is for use as a tire sidewall, the elastomer may comprise at least one essentially saturated diene elastomer, in particular at least one EPDM copolymer, which may for example be used alone or in a mixture with one or more of the highly unsaturated diene elastomers.

The modified elastomer composition containing a vulcanizing system can for example be calendered, for example in the form of thin slabs (thickness of 2 to 3 mm) or thin sheets of rubber in order to measure its physical or mechanical properties, in particular for laboratory characterization, or alternatively can be extruded to form rubber profiled elements used directly, after cutting or assembling to the desired dimensions, as a semi-finished product for tires, in particular as treads, plies of carcass reinforcements, sidewalls, plies of radial carcass reinforcements, beads or chaffers, inner tubes or air light internal rubbers for tubeless tires.

The invention provides a hydrolysable silane of the formula:

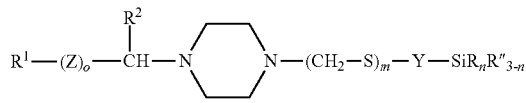

wherein each R represents a hydrolysable group; each R" represents a hydrocarbyl group having 1 to 8 carbon atoms; n=1 to 3; Y represents a divalent organic spacer linkage having 1 to 20 carbon atoms; m=0 or 1; the piperazine ring ("Pip") is optionally substituted on his carbon atoms and bonded through its nitrogen atoms; Z represents an oxygen or sulphur atom; o is 0 or 1; $R^1$ represents a hydrocarbyl or substituted hydrocarbyl group having 1 to 20 carbon atoms: $R^2$ represents hydrogen or a hydrocarbyl or substituted hydrocarbyl group having 1 to 8 carbon atoms and m+o is 1 or 2.

Preferably, Z represents a sulphur atom and R1 represents a group of the formula —Y'—SiRpR"3-p wherein Y' represents a divalent organic spacer linkage having 1 to 20 carbon atoms; each R represents a hydrolysable group; each R" represents a hydrocarbyl group having 1 to 8 carbon atoms; and p=1 to 3.

Preferably, m=1 and Y and Y' each represent an alkylene group having 2 to 6 carbon atoms.

Preferably, Z represents an oxygen atom and R1 represents a hydrocarbyl group having 1 to 8 carbon atoms.

Preferably, m=0 and Y represents an alkylene group having 2 to 6 carbon atoms.

Preferably, R2 represents hydrogen.

Preferably, the 2-, 3-, 5- and 6-positions on the piperazine ring are unsubstituted.

Preferably, each group R is an alkoxy group having 1 to 4 carbon atoms.

Preferably, n=3 and p if present is 3 too.

The invention extends to the hydrolysable silane of the formula: (EtO)3Si(CH2)3SCH2PipCH2S(CH2)3Si(OEt)3 where Et represents an ethyl group.

The invention extends to the hydrolysable silane of the formula

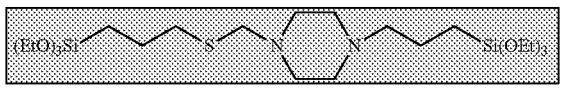

where Et represents an ethyl group.

The invention provides the hydrolysable silane of the formula

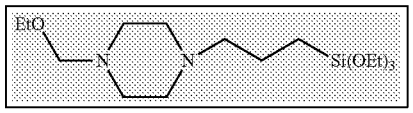

where Et represents an ethyl group.

Preferably, the silane is partially hydrolysed and condensed into oligomers containing siloxane linkages.

The invention provides a process for the preparation of a hydrolysable silane of the formula

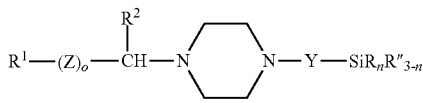

in which each R represents a hydrolysable group; each R" represents a hydrocarbyl group having 1 to 8 carbon atoms; n=1 to 3; Y represents a divalent organic spacer linkage having 1 to 20 carbon atoms; The piperazine ring ("Pip") is optionally substituted and bonded through its nitrogen atoms; Z represents an oxygen or sulphur atom; o is 0 or 1; $R^1$ represents a hydrocarbyl or substituted hydrocarbyl group having 1 to 20 carbon atoms and $R^2$ represents hydrogen or a hydrocarbyl or substituted hydrocarbyl group having 1 to 8 carbon atoms, characterised in that a 1-silylalkyl-1,4-piperazine of the formula H-Pip-Y—SiR$_n$R"$_{3-n}$ wherein R, R", n, and Y are defined as above is reacted with an aldehyde of the formula $R^2$—CHO wherein $R^2$ represents hydrogen or a hydrocarbyl or substituted hydrocarbyl group having 1 to 8 carbon atoms and an alcohol or thiol of the formula $R^1$ZH wherein Z represents an oxygen or sulphur atom; and $R^1$ represents a hydrocarbyl or substituted hydrocarbyl group having 1 to 20 carbon atoms.

The invention provides a process for the preparation of a hydrolysable silane of the formula

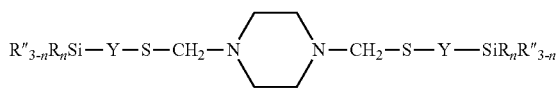

in which each R represents a hydrolysable group; each R" represents a hydrocarbyl group having 1 to 8 carbon atoms; n=1 to 3; and Y represents a divalent organic spacer linkage having 1 to 20 carbon atoms, characterised in that a thioalkyl alkoxysilane of the formula HS—Y—SiR$_n$R"$_{3-n}$ wherein R, R", n, and Y are defined as above is reacted with piperazine and formaldehyde.

The invention provides a process for modifying a polymeric material having a carbon backbone containing carbon-to-carbon unsaturation by reaction with a hydrolysable silane, characterised in that the hydrolysable silane is a hydrolysable silane as defined above.

Preferably, the polymeric material is a diene elastomer.

The invention provides a diene elastomer composition comprising a diene elastomer, a hydrolysable silane and a curing agent for the diene elastomer, characterised in that the hydrolysable silane is a hydrolysable silane as defined above.

The invention provides a composition as defined above characterised in that the hydrolysable silane is present at 0.5 to 15.0% by weight based on the diene elastomer.

Preferably, a filler is present in the composition, whereby the hydrolysable silane acts as a coupling agent between the filler and the diene elastomer.

Preferably, the filler is silica.

The curing agent for the diene elastomer is preferably sulfur or a sulfur compound.

The invention provides a process for the production of a rubber article characterized in that an elastomer composition as defined above is shaped and cured.

Preferably, the elastomer composition is cured at a temperature in the range 130° C. to 180° C.

The invention provides the use of a silane as defined above as a coupling agent for a diene elastomer composition containing a filler.

The invention extends to a process as defined above characterised in that the polymeric material is carbon fibre or carbon black.

EXAMPLE 1

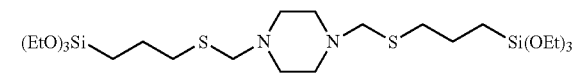

Detailed synthesis of N,N'-bis(3-triethoxysilylpropylthiomethyl)piperazine. A 500 ml two necked round bottom flask, fitted with a condenser, nitrogen sweep and magnetic stirrer, was charged with 8.6 g piperazine, 6.0 g paraformaldehyde and 100 ml toluene. The mixture was refluxed for 4 h and formed water was removed using a Dean-Stark set-up. Then, 47.8 g 3-mercaptopropyltriethoxysilane was added and reflux was maintained for 1 h 30. Solids were separated by filtration through paper filter while solvent and volatile compounds were evaporated in vacuo. Both formation of the thiomethylamine structure and preservation of the triethoxysilane fragment were confirmed by nuclear magnetic resonance.

EXAMPLE 2

Rubber goods were prepared according to the procedure described below for example 1 and comparative examples C1 and C2, using the ingredients described below.

The amounts expressed in parts per hundred parts of rubber (phr) are described in table 1.

NR TSR 10, CV60—Natural rubber Technical Standard Rubber, purity grade 10, Constant viscosity (CV) 60 m.u. (Mooney unit)

Silica—Zeosil® 1165MP from Rhodia

Silane 1—Bis-(triethoxysilylpropyl)-tetrasulfane—Z-6940 by Dow Corning

Silane 2—N,N'-bis(triethoxysilylpropylthiomethyl)-piperazine

ACST—Stearic Acid

ZnO—Zinc Oxide

6PPD—N-1,3-dimethylbutyl-N-phenyl-para-phenylenediamine from Rhein Chemie

S—Elemental sulphur from Sigma Aldrich

CBS—N-cyclohexyl-2-benzothiazyl sulfenamide ("Santocure® CBS" from Flexsys)

N234—Conventional carbon black according to ASTM D1765

DPG 80%—diphenylguanidine supported on EPDM at 80% active material from Rhein Chemie (Vulkanox® 4020/LG)

TABLE 1

| | example | | |
|---|---|---|---|
| | C1 | 2 | C2 |
| NR SMR 10 CV60 | 100.00 | 100.00 | 100.00 |
| Silica - Z1165MP | 57.00 | 57.00 | |

TABLE 1-continued

| | example | | |
|---|---|---|---|
| | C1 | 2 | C2 |
| Silane 1 | 5.00 | | |
| Silane 2 | | 6.42 | |
| Carbon black N234 | | | 45.00 |
| ACST | 2.50 | 2.50 | 2.50 |
| ZnO | 3.00 | 3.00 | 3.00 |
| 6PPD | 2.00 | 2.00 | 2.00 |
| S | 2.00 | 2.05 | 1.50 |
| DPG | 1.00 | | |
| CBS | 1.80 | 2.16 | 1.00 |

In a comparative example C1, silane 1 was used as reference coupling system well known by those skilled in the art for silica and diene elastomers.

The comparative example C2 was a standard natural rubber formulation for tyre treads using carbon black filler.

During a first non-productive phase, the reaction of the natural rubber, filler and when present silane was carried out using thermomechanical kneading in a Banbury mixer. The procedure was as shown in Table 2, which indicates the time of addition of various ingredients. The temperature at the end of mixing was measured inside the rubber after dumping it from the mixer.

TABLE 2

| | Time (seconds) | | | | |
|---|---|---|---|---|---|
| | 0 | 60 | 90 | 150 | 360 |
| Ingredient | Natural rubber | ⅔ Filler (Silane) | ⅓ filler | Ram opening | End mixing |
| Mixer internal probe indicative temperature (° C.) | 80 | 90 | 100 | 160 | 155-165 |

During a second non-productive phase stearic acid, zinc oxide and 6PPD were added to the obtained compound from the first non-productive phase. The mixing was carried out using thermomechanical kneading in a Banbury mixer. The procedure was as shown in Table 3, which indicates the time of addition of various ingredients and the estimated temperature of the mixture at that time.

TABLE 3

| | Time (seconds) | | |
|---|---|---|---|
| | 0 | 30 | 300 |
| Ingredient | Natural rubber | ZnO AcSt 6PPD | End mixing |
| Mixer internal probe indicative temperature (° C.) | 80 | 90 | 155-165 |

The modified natural rubber composition thus produced was milled on a two-roll mill at a temperature of about 70° C. during which milling the curing agents were added (productive phase). The mixing procedure for the productive phase is shown in Table 4.

TABLE 4

| 2 roll mill process step | Number of passes | Roll distance (mm) | Time/action |
|---|---|---|---|
| Heating up rubber | 5 | 4.0 | NA |
| | 1 | 3.5 | NA |
| | 1 | 3.0 | NA |
| | 1 | 2.5 | NA |
| Mixing rubber and additives | NA | 2-2.4 | Form a mantle around one roll add curing additives within 2.0 minutes cut and turn sheet regularly Stop after 6.0 minutes |
| Sheet formation | 3 | 2.5 | roll up |
| | 2 | 5.1 | Roll on first pass 3-ply for second |
| | 1 | 2.3-2.5 | For final sheet for cutting, moulding and curing |

The modified rubber sheet produced was tested as follows. The results of the tests are shown in Table X below.

The rheometry measurements were performed at 160° C. using an oscillating chamber rheometer (i.e., Advanced Plastic Analyzer) in accordance with Standard ISO 3417:1991 (F). The change in rheometric torque over time describes the course of stiffening of the composition as a result of the vulcanization reaction. The measurements are processed in accordance with Standard ISO 3417:1991(F). Minimum and maximum torque values, measured in deciNewtonmeter (dNm) are respectively denoted ML and MH time at a % cure (for example 5%) is the time necessary to achieve conversion of a % (for example 5%) of the difference between the minimum and maximum torque values. The difference, denoted MH-ML, between minimum and maximum torque values is also measured. In the same conditions the scorching time for the rubber compositions at 160° C. is determined as being the time in minutes necessary to obtain an increase in the torque of 2 units, above the minimum value of the torque (Time@2dNm scorch S').

The tensile tests were performed in accordance with ISO Standard IS037:1994(F) using tensile specimen ISO 37—type 2. The nominal stress (or apparent stresses, in MPa) at 10% elongation (M10), 100% elongation (M100) and elongation (M250 or M300) are measured at 10%, 100% and 250% or 300% of elongation. Breaking stresses (in MPa) are also measured. Elongation at break (in %) was measured according to Standard ISO 37. High values of Elongation at break are preferred. Preferably the Elongation at break is at least 300%. All these tensile measurements are performed under normal conditions of temperature and relative humidity in accordance with ISO Standard ISO 471. The ratio of M300 to M100 correlates with tread wear resistance of a tyre made from the rubber composition, with an increase in M300/M100 ratio indicating potential better tread wear resistance.

The dynamic properties were measured on a viscoanalyser (Metravib VA4000), in accordance with ASTM Standard D5992-96.

Strain sweep: The response of a sample of vulcanized composition (thickness of 2.5 mm and a cross-section of 40 mm$^2$), subjected to an alternating single sinusoidal shearing stress, at a frequency of 10 Hz, under a controlled temperature of 55° C. is recorded. Scanning is performed at amplitude of deformation of 0.150% the maximum observed value of the loss factor tan d is recorded, the value being denoted tan δ 6%. The tan δ 6% value is well correlated to the rolling resistance of the tire, the lower the tan δ 6% the lower the rolling resistance is, the better the tire performance will be. G'$_0$ is the elastic modulus measured at very low strain, when the behaviour is linear with the stress. $G'_{max}$ is the elastic modulus at 50% strain. Dynamical properties have been recorded after a first strain sweep ($G'_0$) from 0.1 to 50%, then the second strain sweep from 50% to 0.1% has been also recorded. The difference between the modulus at first strain sweep and the modulus after the return to low strain ($G'_0$ return) is denoted $\Delta G'_0$ which is well correlated to the handling stability of the tire under stress. The difference between $G'_0$ return and $G'_{max}$ after the second strain sweep is denoted $\Delta G'$ return. The tan δ 6%, second strain sweep value corresponds to the maximum of the loss factor tan (δ) during the second strain sweep. A reduction in both tan δ 6% and tan δ 6%, second strain sweep is well correlated to a decrease in the rolling resistance of a tire manufactured from the rubber composition.

Temperature sweep: The response of a sample of vulcanized composition (thickness of 2.5 mm, height of 14 mm and length of 4.0 mm), subjected to an alternating single sinusoidal shearing stress, at a frequency of 10 Hz, under a controlled displacement of 1.25 micron. The sample is placed at room temperature and cooled down to −100° C. with a rate of 5° C./min. The temperature is then stabilised at −100° C. for 20 minutes to allow the sample to be at an equilibrium temperature state. The temperature is then increased up to 100° C. at a rate of 5° C./min. The loss factor and the stiffness, giving the modulus and the tan (δ). The tan $δ_{max}$ and/or the value at 0° C. (tan $δ_{0° C.}$) is related to the wet skid performances. An increase in the tan $δ_{max}$ and in the tan (δ) value at 0° C. (tan $δ_{0° C.}$) is indicative of improved wet skid performance.

The Shore A hardness was measured according to ASTM D2240-02b.

TABLE 5

| | Example | | |
|---|---|---|---|
| | C1 | 1 | C2 |
| Mmax (m.u.) | 53 | 56 | 54 |
| ML1 + 4 (m.u.) | 37 | 36 | 34 |
| ML (dNm) | 0.9 | 1.2 | 0.9 |
| MH (dNm) | 16.3 | 14.0 | 13.8 |
| MH − ML (dNm) | 15.4 | 12.8 | 12.8 |
| $G'_0$ (Pa) | 2.13 | 1.94 | 5.05 |
| $G'_{max}$ (Pa) | 1.277 | 1.147 | 1.159 |
| $\Delta G'$ (Pa) | 0.853 | 0.793 | 3.890 |
| Tan d 6%, second strain sweep | 0.058 | 0.064 | 0.202 |
| Tan $d_{0° C.}$ | 0.160 | 0.151 | 0.132 |
| Tan $d_{max}$ | 1.195 | 1.243 | 0.894 |
| M100 (MPa) | 4.4 | 3.7 | 3.2 |
| M300 (MPa) | 20.6 | 19.7 | 15.9 |
| M300/M100 | 4.7 | 5.3 | 5.0 |
| Tensile break (MPa) | 26.9 | 29.1 | 27.7 |
| Elong max (%) | 383 | 425 | 477 |
| Shore A | 56 | 55 | 54 |

Comparative example C1 and example 1 showed very similar M300 properties, and viscoelastic properties (G'0, tan d 6%) translating the ability of silane 2 to couple with Natural rubber efficiently.

Example 1 showed lower crosslinking density (MH-ML) leading to underestimation of the mechanical and viscoelastic properties that should be better than for comparative example C1.

Example 1 showed higher M300/M100, elongation at break and stress at break than comparative example C1 leading to a potential better tread wear performance than comparative example C1.

Example 1, as comparative example C1, showed a significantly reduced tan d 6% as compared to comparative example C2 leading to a significant potential reduction of fuel consumption through rolling resistance reduction. Example 1 exhibited overall a better balance of performance than both comparative example C1 and C2 with a low rolling resistance and a good abrasion resistance.

EXAMPLE 3

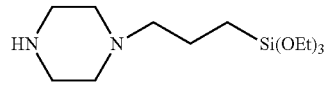

Detailed synthesis of N-(3-triethoxysilylpropyl)piperazine. A 500 ml three necked round bottom flask, fitted with a condenser, nitrogen sweep and magnetic stirrer and an addition funnel containing 48.2 g 3-chloropropyltriethoxysilane, was charged with 68.5 g piperazine, 170.7 g toluene and 30.5 g diazabicycloundecene (DBU). 3-chloropropyltriethoxysilane was slowly added at room temperature to the mixture of amines in toluene, under vigorous stirring. Reaction mixture was then refluxed for 5 hours under nitrogen atmosphere. Solid by-products were filtered off and volatiles removed under vacuo (75° C., 50 mbar) affording the mono silylated piperazine as a liquid. Quantitative monoalkylation of piperazine was confirmed by nuclear magnetic resonance spectroscopy, as well as preservation of the triethoxysilyl fragment (90%).

EXAMPLE 4

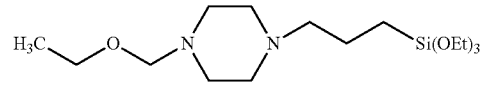

Detailed synthesis of N-(Ethoxymethyl)-N'-(3-triethoxysilylpropyl)piperazine. A 100 ml two necked round bottom flask, fitted with a condenser, nitrogen sweep and magnetic stirrer, was charged with 26.2 g N-(3-triethoxysilylpropyl) piperazine, 2.7 g paraformaldehyde and 25.2 g ethanol. The mixture was refluxed for 2 h 30 under nitrogen atmosphere. Volatiles were removed in vacuo (75° C., 40 mbar). Formation of the ethoxymethylamine structure with a 85% conversion rate was confirmed by nuclear magnetic resonance, as well as preservation of the triethoxysilyl functionality (65%).

The invention claimed is:

1. A hydrolysable silane of the formula

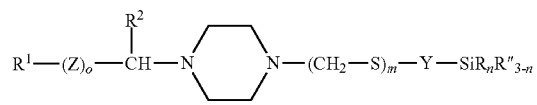

wherein each R represents a hydrolysable group; each R" represents a hydrocarbyl group having 1 to 8 carbon atoms; n =1 to 3; Y represents a divalent organic spacer linkage having 1 to 20 carbon atoms; m =0 or 1; the piperazine ring ("Pip") is optionally substituted on his carbon atoms and bonded through its nitrogen atoms; Z represents an oxygen or sulphur atom; o is 0 or 1; $R^1$ represents a hydrocarbyl or substituted hydrocarbyl group having 1 to 20 carbon atoms: $R^2$ represents hydrogen or a hydrocarbyl or substituted hydrocarbyl group having 1 to 8 carbon atoms and m+o is 1 or 2.

2. A hydrolysable silane according to claim 1, characterised in that Z represents a sulphur atom and $R^1$ represents a group of the formula —Y'—$SiR_pR''_{3-p}$ wherein Y' represents a divalent organic spacer linkage having 1 to 20 carbon atoms; each R represents a hydrolysable group; each R" represents a hydrocarbyl group having 1 to 8 carbon atoms; and p =1 to 3.

3. A hydrolysable silane according to claim 2, characterised in that m =1 and Y and Y' each represent an alkylene group having 2 to 6 carbon atoms.

4. A hydrolysable silane according to claim 1, characterised in that Z represents an oxygen atom and $R^1$ represents a hydrocarbyl group having 1 to 8 carbon atoms.

5. A hydrolysable silane according to claim 1, characterised in that m =0 and Y represents an alkylene group having 2 to 6 carbon atoms.

6. A hydrolysable silane according to claim 1, characterised in that $R^2$ represents hydrogen.

7. A hydrolysable silane according to claim 1, characterised in that the 2-,3-,5- and 6-positions on the piperazine ring are unsubstituted.

8. A hydrolysable silane according to claim 1, characterised in that each group R is an alkoxy group having 1 to 4 carbon atoms, n =3 and p if present is 3 too, or each group R is an alkoxy group having 1 to 4 carbon atoms and n =3 and p if present is 3 too.

9. A hydrolysable silane according to claim 1, characterised in that the silane is partially hydrolysed and condensed into oligomers containing siloxane linkages.

10. A process for modifying a polymeric material having a carbon backbone containing carbon-to-carbon unsaturation by reaction with a hydrolysable silane, characterised in that the hydrolysable silane is a hydrolysable silane as defined in claim 1.

11. A process according to claim 10, characterised in that the polymeric material is a diene elastomer.

12. A process according to claim 10 characterised in that the polymeric material is carbon fibre or carbon black.

13. A diene elastomer composition comprising a diene elastomer, a hydrolysable silane and a curing agent for the diene elastomer, characterised in that the hydrolysable silane is a hydrolysable silane as defined in claim 1.

14. A composition according to claim 13 characterised in that the hydrolysable silane is present at 0.5 to 15.0% by weight based on the diene elastomer.

15. A composition according to claim 13 characterised in that a filler is present in the composition, whereby the hydrolysable silane acts as a coupling agent between the filler and the diene elastomer.

16. A composition according to claim 13 characterised in that the curing agent for the diene elastomer is sulfur or a sulfur compound.

17. A process for the production of a rubber article characterized in that an elastomer composition according to claim 13 is shaped and cured.

18. A hydrolyzable silane selected from the group consisting of $(EtO)_3Si(CH_2)_3SCH_2PipCH_2S(CH_2)_3Si(OEt)_3$, $(EtO)_3Si(CH_2)_3SCH_2Pip(CH_2)_3Si(OEt)_3$, and $EtOCH_2Pip(CH_2)_3Si(OEt)_3$, where Pip is equal to

19. A process for the preparation of a hydrolysable silane of the formula

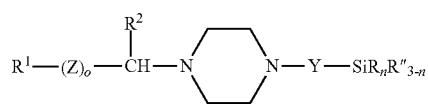

in which each R represents a hydrolysable group; each R" represents a hydrocarbyl group having 1 to 8 carbon atoms; n =1 to 3; Y represents a divalent organic spacer linkage having 1 to 20 carbon atoms; The piperazine ring ("Pip") is optionally substituted and bonded through its nitrogen atoms; Z represents an oxygen or sulphur atom; o is equal to 1;

$R^1$ represents a hydrocarbyl or substituted hydrocarbyl group having 1 to 20 carbon atoms and $R^2$ represents hydrogen or a hydrocarbyl or substituted hydrocarbyl group having 1 to 8 carbon atoms, characterised in that a 1-silylalkyl-1,4-piperazine of the formula H-Pip-Y—$SiR_nR''_{3-n}$ wherein R, R", n, and Y are defined as above is reacted with an aldehyde of the formula $R^2$—CHO wherein $R^2$ represents hydrogen or a hydrocarbyl or substituted hydrocarbyl group having 1 to 8 carbon atoms and an alcohol or thiol of the formula $R^1$ZH wherein Z represents an oxygen or sulphur atom; and $R^1$ represents a hydrocarbyl or substituted hydrocarbyl group having 1 to 20 carbon atoms.

20. A process for the preparation of a hydrolysable silane of the formula

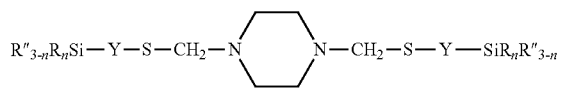

in which each R represents a hydrolysable group; each R" represents a hydrocarbyl group having 1 to 8 carbon atoms; n =1 to 3; and Y represents a divalent organic spacer linkage having 1 to 20 carbon atoms, characterised in that a thioalkyl alkoxysilane of the formula HS—Y—$SiR_nR''_{3-n}$ wherein R, R", n, and Y are defined as above is reacted with piperazine and formaldehyde.

* * * * *